(12) United States Patent
Karkanias et al.

(10) Patent No.: US 8,287,281 B2
(45) Date of Patent: Oct. 16, 2012

(54) MEMORY TRAINING VIA VISUAL JOURNAL

(75) Inventors: Chris Demetrios Karkanias, Sammamish, WA (US); Stephen E. Hodges, Cambridge (GB); Emma L. Berry, Herts (GB); Georgina E. Browne, Cambridge (GB); Hilary Lyndsay Williams, Cambridge (GB); Kenneth R. Wood, Cambridge (GB); Samuel Gavin Smyth, Huntingdon (EP); David Alexander Butler, Great Cambourne (GB)

(73) Assignee: Microsoft Corporation, Redmond, WA (US)

( * ) Notice: Subject to any disclaimer, the term of this patent is extended or adjusted under 35 U.S.C. 154(b) by 1028 days.

(21) Appl. No.: 11/567,459

(22) Filed: Dec. 6, 2006

(65) Prior Publication Data

US 2008/0138783 A1    Jun. 12, 2008

(51) Int. Cl.
*G09B 19/00* (2006.01)
(52) U.S. Cl. .......... 434/236; 434/350; 434/238
(58) Field of Classification Search .......... 434/350, 434/236, 238
See application file for complete search history.

(56) References Cited

U.S. PATENT DOCUMENTS

| 4,273,540 | A |   | 6/1981  | Dill |
|-----------|---|---|---------|------|
| 5,275,159 | A |   | 1/1994  | Griebel |
| 5,307,263 | A |   | 4/1994  | Brown |
| 5,389,965 | A | * | 2/1995  | Kuzma ............... 348/14.05 |
| 5,447,164 | A |   | 9/1995  | Shaya et al. |
| 5,538,432 | A |   | 7/1996  | Dondero et al. |
| 5,664,109 | A |   | 9/1997  | Johnson et al. |
| 5,808,670 | A | * | 9/1998  | Oyashiki et al. ............ 348/143 |
| 6,032,119 | A |   | 2/2000  | Brown et al. |
| 6,067,399 | A | * | 5/2000  | Berger ............... 386/280 |
| 6,208,379 | B1| * | 3/2001  | Oya et al. ............... 348/211.11 |
| 6,211,787 | B1| * | 4/2001  | Yoshiike et al. ........... 340/573.1 |
| 6,216,228 | B1| * | 4/2001  | Chapman et al. ............ 713/176 |
| 6,228,028 | B1|   | 5/2001  | Klein et al. |
| 6,246,992 | B1|   | 6/2001  | Brown |
| 6,282,441 | B1|   | 8/2001  | Raymond et al. |
| 6,373,507 | B1|   | 4/2002  | Camara et al. |
| 6,626,678 | B2|   | 9/2003  | Forbes |
| 6,632,174 | B1|   | 10/2003 | Breznitz |
| 6,727,935 | B1| * | 4/2004  | Allen et al. ............... 348/14.03 |
| 7,046,924 | B2|   | 5/2006  | Miller et al. |
| 7,234,117 | B2| * | 6/2007  | Zaner et al. ............... 715/758 |

(Continued)

FOREIGN PATENT DOCUMENTS

EP    0559422 A1    9/1993

(Continued)

OTHER PUBLICATIONS

Aizawa, K. "Digitizing Personal Experience: Capture and Retrieval of Life Log" 11th International Conference on Multi Media Modeling (MMM 2005), Jan. 12-14, 2005, Melbourne, Australia. IEEE Computer Society 2005.*

(Continued)

*Primary Examiner* — Robert J Utama

(57) ABSTRACT

A system that can enhance cognitive ability by viewing sequences of images captured during an event is disclosed. For example, the innovation can employ captured event sequences to improve failing memories in patients with a diagnosed memory condition such as acquired brain injury or neurodegenerative disease such as Alzheimer's disease. These event sequences can be captured in the point-of-view of a user (e.g., first person) as well as from a third person or other monitoring location (e.g., car).

20 Claims, 12 Drawing Sheets

U.S. PATENT DOCUMENTS

| | | | |
|---|---|---|---|
| 7,242,318 | B2 | 7/2007 | Harris |
| 7,257,832 | B2 | 8/2007 | Beane et al. |
| 7,653,259 | B2* | 1/2010 | Pilu .............................. 382/276 |
| 7,693,729 | B2 | 4/2010 | Yankelevitz et al. |
| 7,860,287 | B2 | 12/2010 | Zahlmann et al. |
| 7,983,933 | B2 | 7/2011 | Karkanias et al. |
| 2001/0044588 | A1 | 11/2001 | Mault |
| 2002/0171669 | A1 | 11/2002 | Meron et al. |
| 2003/0036683 | A1 | 2/2003 | Kehr et al. |
| 2003/0063072 | A1* | 4/2003 | Brandenberg et al. ........ 345/173 |
| 2003/0133614 | A1 | 7/2003 | Robins et al. |
| 2003/0208378 | A1 | 11/2003 | Thangaraj et al. |
| 2004/0025030 | A1 | 2/2004 | Corbett-Clark et al. |
| 2004/0175683 | A1* | 9/2004 | Duffy et al. ................... 434/258 |
| 2004/0201697 | A1 | 10/2004 | Klein |
| 2005/0149869 | A1 | 7/2005 | Kehr et al. |
| 2005/0159970 | A1* | 7/2005 | Buyukkokten et al. ............ 705/1 |
| 2005/0182664 | A1 | 8/2005 | Abraham-Fuchs et al. |
| 2005/0251011 | A1 | 11/2005 | Zahlmann et al. |
| 2006/0089542 | A1 | 4/2006 | Sands |
| 2006/0111620 | A1 | 5/2006 | Squilla et al. |
| 2006/0117378 | A1* | 6/2006 | Tam et al. .......................... 726/3 |
| 2006/0190827 | A1* | 8/2006 | Zaner et al. .................... 715/751 |
| 2006/0190828 | A1 | 8/2006 | Zaner et al. |
| 2007/0016443 | A1 | 1/2007 | Wachman et al. |
| 2007/0206510 | A1 | 9/2007 | Morris et al. |
| 2007/0260492 | A1 | 11/2007 | Feied et al. |
| 2007/0292012 | A1 | 12/2007 | Brandon et al. |
| 2008/0052112 | A1 | 2/2008 | Zahlmann et al. |
| 2008/0119958 | A1 | 5/2008 | Bear et al. |
| 2008/0140444 | A1 | 6/2008 | Karkanias et al. |
| 2008/0183049 | A1 | 7/2008 | Karkanias et al. |

FOREIGN PATENT DOCUMENTS

| | | |
|---|---|---|
| JP | 2002-064815 | 2/2002 |
| KR | 10-2000-0076025 | 12/2000 |
| KR | 10-2001-0050099 | 6/2001 |
| KR | 10-2004-0012155 | 2/2004 |
| KR | 10-2005-0016741 | 2/2005 |
| KR | 10-2006-0032243 | 4/2006 |
| KR | 10-2006-0064885 | 6/2006 |
| WO | WO0171636 | 9/2001 |
| WO | WO2005120071 | 12/2005 |

OTHER PUBLICATIONS

Aizawa et al. "Efficient Retrieval of Life Log Based on Context and Content" CARPE'04, Oct. 15, 2004, New York, New York, USA.*

Aizaw et al. "Summarizing Wearable Video" Proc. Intl. Conf. of ICIP 2001, vol. 3, (Oct. 2001), 398-401.*

Aizawa et al "Wearable Imaging System for Summarizing Personal Experiences" Proceedings of the 2003 International Conference on Multimedia and Expo—vol. 2 table of contents pp. 45-48, 2003.*

Megumu Tsuchikawa, "Experience-Sharing System Using Ubiquitous Sensing Environments" UCS 2004, LNCS 3598, pp. 90-103, 2005.*

International Search Report and Written Opinion dated May 7, 2008 for PCT Application Serial No. PCT/US2007/086671, 10 Pages.

IT Management News, CNET Networks, Inc., 2005 <http://news.zdnet.co.uk/itmanagement/0,1000000308,39209713,00.htm>, last accessed on Dec. 6, 2006, 3 pages.

Snap Happy Sense, Adaptive Information Cluster 2006 <http://www.adaptiveinformation.ie/?module=datalistdetail&itemid=abac0774-5104-41a7-881c-84a50236d1e2>, last accessed on Dec. 6, 2006, 2 pages.

Steve Hodges, et al. Sensors and Devices, Microsoft Corporation 2006, <http://research.microsoft.com/sendev/projects/sensecam/> last accessed on Dec. 6, 2006, 4 pages.

Daniel Ashbrook, et al. Capturing Experiences Anytime, Anywhere, IEEE Pervasive Computing 2006, <http://csdl2.computer.org/persagen/DLAbsToc.jsp?resourcePath=/dl/mags/pc/&toc=comp/mags/pc/2006/02/b2toc.xml&DOI=10.1109/MPRV.2006.26> last accessed on Dec. 6, 2006, 3 pages.

Chilean OA dated Nov. 20, 2009 for CL Application Serial No. 3506-2007, 2 pages.

CN OA dispatched Oct. 9, 2010 for Chinese Patent Application No. 2007800454290, 15 pages.

Aizawa. Digitizing Personal Experiences: Capture and Retrieval of Life Log. Proceedings of the 11th International Multimedia Modelling Conference (MMM '05), last accessed Oct. 28, 2010, 6 pages.

Aizawa, et al. Efficient Retrieval of Life Log Based on Context and Content. CARPE'04, Oct. 15, 2004, ACM 1-58113-932-2/04/0010, 10 pages.

Sawahata, et al. Wearable Imaging System for Summarizing Personal Experiences. ICME 2003, IEEE 0-7803-7965-9/03, last accessed Oct. 28, 2010, 8 pages.

Aizawa, et al. Summarizing Personal Video. IEEE 0-7803-6725-1/01, last accessed Oct. 28, 2010, 4 pages.

International Search Report and Written Opinion regarding PCT Application No. PCT/US2007/086596 dated May 19, 2008.

International Preliminary Report on Patentability regarding PCT Application No. PCT/US2007/086596 dated Jun. 18, 2009.

"Penn Medicine to Use InforMedix's Med-eMonitor System in Stroke Prevention Pilot Program", Business Wire Press Release dated Aug. 22, 2006.

International Search Report and Written Opinion regarding PCT Application No. PCT/US2008/052719 dated Jul. 17, 2008.

International Preliminary Report on Patentability regarding PCT Application No. PCT/US2008/052719 dated Aug. 13, 2009.

International Preliminary Report on Patentability regarding PCT Application No. PCT/US2007/086671 dated Jun. 18, 2009.

Office Action from the United States Patent and Trademark Office regarding U.S. Appl. No. 11/567,455 dated Dec. 28, 2009.

Office Action from the United States Patent and Trademark Office regarding U.S. Appl. No. 11/567,455 dated Jun. 25, 2010.

Office Action from the United States Patent and Trademark Office regarding U.S. Appl. No. 11/567,455 dated Oct. 4, 2010.

Office Action from the United States Patent and Trademark Office regarding U.S. Appl. No. 11/669,831 dated Dec. 22, 2009.

Office Action from the United States Patent and Trademark Office regarding U.S. Appl. No. 11/669,831 dated Apr. 30, 2010.

Office Action from the State Intellectual Property Office of the People's Republic of China regarding Application No. 200780045429.0 dated Feb. 29, 2012.

Office Action from the Israeli Patent Office regarding Application No. 198553 dated Dec. 29, 2011.

* cited by examiner

MEMORY TRAINING VIA VISUAL JOURNAL

BACKGROUND

Human memory is often all too fallible—as such, many people frequently forget things that they intend to do, and often find it hard to recall the details around what has been previously done. Of course, for those with clinically diagnosed memory disorders—which are by their nature more severe than those found in the average population—these issues are particularly troublesome. One example of such a disorder is acquired brain injury, which occurs either through a disease with lasting effect on brain tissue, or a traumatic incident like a car accident. Another example, perhaps of more significance in an aging population, is neurodegenerative disease which is essentially an illness which damages the brain such that there is no possibility of recovery. Probably, the most prevalent neurodegenerative disease is Alzheimer's disease.

As stated above, two broad categories of conditions that cause memory loss or a decrease in memory retention in humans are neurodegenerative diseases and acquired or traumatic brain injury. To date, medical advances have shown very limited success in treating either of these categories of conditions. For example, attempts have been made to employ external memory aids to assist in treatment. However, these attempts have also been extremely limited in their success.

Neurodegenerative disease refers to a condition that affects brain function. More particularly, neurodegenerative diseases often result from a deterioration of neurons in the brain. There are many known neurodegenerative diseases and conditions that affect memory function. Alzheimer's disease and Lewy Body dementia are but two well known neurological diseases. Although recent medical advances have yielded limited success in treating these two diseases with medication, no medical treatment has been proven to assist in addressing memory loss prompted by these diseases as well as other known dementias.

One of the most common acquired brain injuries is amnesia which refers to a condition where the memory is disturbed. Amnesia can be caused in a number of ways including, trauma, disease and drug/alcohol use. Additionally, amnesia can be spontaneous, e.g., transient global amnesia, which is most common in middle-aged to elderly people. Unfortunately, to date, there are not any effective medical treatments available for acquired brain injuries such as amnesia. Rather, treatment for amnesia is often related to the root cause of the injury. Sedation, affection, psychiatric treatment, hypnosis and abstinence (in the case of drug/alcohol related) are examples of ways to cope with amnesia today.

The effects of acquired brain injuries, neurodegenerative diseases and aging in general vary greatly from patient to patient. In a relatively moderate form, there may be little noticeable effect—perhaps a patient will be frustrated from time-to-time at their inability to organize themselves as well as in the past. At a more extreme level, a patient may suffer from a near complete inability to remember. Patients with moderate to severe memory problems may fail to remember future intentions, such as buying milk, or making and keeping appointments (e.g., prospective memory).

Prospective memory problems clearly have a large impact on the ability of a patient to look after themselves on a day-to-day basis. A failure of past (e.g., retrospective) memory, however, and in particular episodic or autobiographical memory (e.g., the memory of things the patient has done, as opposed to their semantic memory for factual information) is actually critical for a patient to enjoy any real quality of life. This is firstly because nearly all future actions are based on past experiences, so practical day-to-day planning is very difficult when autobiographical memory is impaired. Secondly, and perhaps more importantly, a memory of past experiences is critical to a patient's 'self-concept'. For example, without a memory of shared experiences it is very hard to maintain any kind of relationship, whether it is professional, social or personal. This in turn frequently affects the patient's self-esteem, which can have significant effects on their well-being.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed and claimed herein, in one aspect thereof, comprises a system that can enhance cognitive ability by viewing sequences of images captured during an event. For example, one key issue addressed by this disclosure is the application of captured event sequences to improve failing memories in patients with a diagnosed memory condition such as acquired brain injury or neurodegenerative disease such as Alzheimer's disease. As well, the system can be employed to increase memory function and recall of details related to events experienced by a user. These event sequences can be captured in the point-of-view of a user (e.g., first person) as well as from a third person or other monitoring location (e.g., on top of a car dashboard).

The event image capture concepts of the innovation disclose and suggest recording information encountered during events within one's daily activities. In order to trigger image capture, the innovation discloses use of physiological as well as environmental sensors, e.g., blood pressure, mood, body temperature, external temperature, location, motion, lighting as well as time-based mechanisms. In operation, the information gathered via the sensory mechanisms can be used to annotate images (and sequences thereof). These annotations can be used to enhance location and playback of images in the course of training, therapy, recall, etc.

The innovation effectively suggests and discloses capture of images (and video) related to the daily activities of a user, essentially, establishing a super-journal of a day or of events encountered within a day (or other period of time). This can be especially useful as an aid with patients that have deteriorating, limited and/or impaired memory capacity as working through a paper journal can be very tedious.

The innovation discloses using a high-fidelity rendition of a day rather than focusing on what was manually written down by a user to enhance or improve memory capacity. It will be appreciated that memory works in an associative way in that a single picture of an event (e.g., vacation) or a sequence of images or video which relate to part of the event can be shown to trigger recall of the complete event (e.g., vacation). Thus, the innovation can have a high ability to remind people based upon images received even if they have a very limited amount of memory. Moreover, these results are sustainable so the memory recall continues proportional to use.

In a health care context, the innovation can be used, for example, in a situation of autism where outbursts are most often inexplicable. In other words, it is often that the events leading to an outburst cannot be explained. In another example, the innovation can be used to monitor actions of an individual with anger management issues. By using the innovation, not only will the subject view be captured but, also other's views within the room or proximity can be captured to further assist in explaining the situation and to prompt recall by the person affected.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
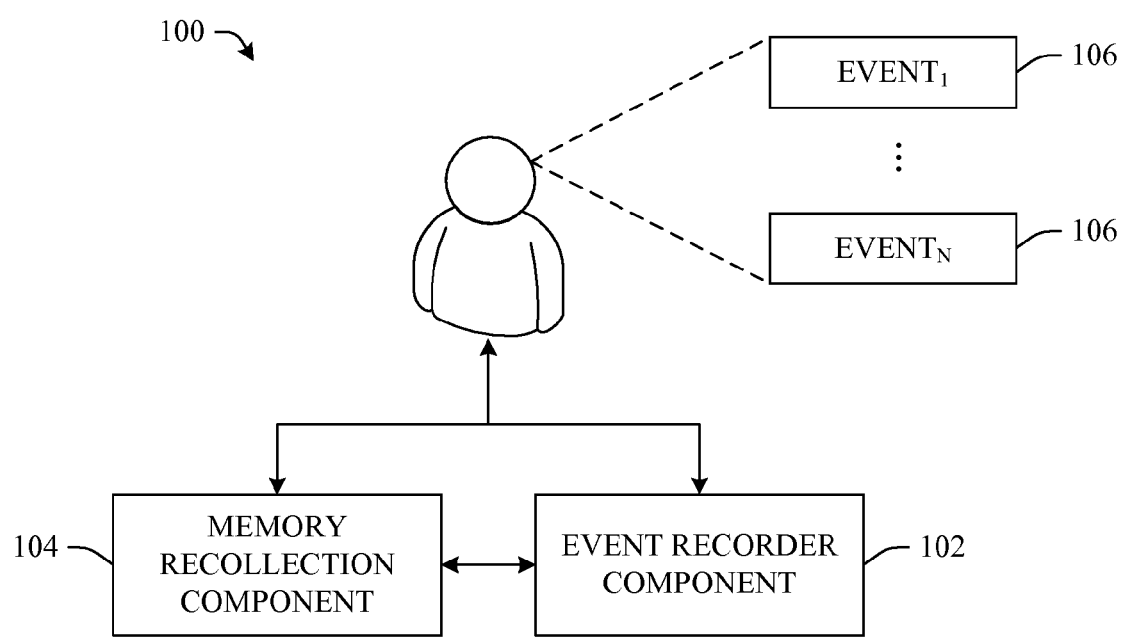
FIG. 1 illustrates an example system that facilitates employing event image sequences in memory function training and/or rehabilitation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

As used herein, the term to "infer" or "inference" refer generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

Referring initially to the drawings, FIG. 1 illustrates a system 100 that enhances memory function and performance through the use of visual cues. As illustrated, generally, the system 100 includes an event recorder component 102 and a memory recollection component 104. In operation, the event recorder component 102 can automatically record images related to 1 to N events throughout a user's day (or other specified period of time). It is to be understood that 1 to N events can be referred to individually or collectively as events 106.

In more particular aspects, the event recorder component 102 can be employed to capture images related to a user that suffers from some sort of dementia or acquired brain injury. The granularity and frequency of the captured events can be programmed, pre-programmed or contextually triggered via the event recorder component 102. By way of example, the event recorder component 102 can be equipped with sensors (e.g., light sensors, location sensors, motion sensors) whereby when a change in a designated criterion is detected, an image of the event 106 is captured.

Subsequently, the memory recollection component 104 can be employed to prompt recall of events 106 throughout the period of capture (e.g., hour, day, month). For illustration purposes, it will be understood and appreciated that the memory works in a somewhat associative way. For instance, it is not uncommon that a person cannot recall the order of music tracks on an album or compact disc. However, if a track is heard, oftentimes it is possible to recall the subsequent tracks as a function of the current track. This recall is prompted by the associative manner in which the brain functions. In other words, once a track is completed, memory is triggered and the person is able to recall the next and sometimes even subsequent tracks.

In accordance with the innovation, when image sequences are reviewed, the viewer can get a strong stimulus to recall which means that they are likely to remember details of the day or period of capture, including things not recorded in the images such as what people said, what food was eaten, etc. Additionally, if a sequence of images is reviewed repeatedly, following a suitable schedule (e.g., watching it four times every two days) then that repeated act of recall stimulation can act to consolidate an ability to recall. Thereafter, an individual may recall the details of that event unaided, for example, without having to watch the image sequence again.

In aspects, memory recall can be achieved for example by showing still images in rapid succession in a 'slide-show format'. Additionally, the images can be complimented with other data, for example ambient audio recorded at the time of the images or other audio (such as a soundtrack), to complement the visual nature of the playback.

Similarly, these events can also trigger recall of other associated events and information. By way of further example, hearing a track of an album can not only trigger the next track on the album but, can also trigger recall of the artist name, other songs by the author. Additionally, hearing the song can also trigger thoughts of outside events, people, places, etc. Essentially, this association can contribute to memory training and enhancement.

With reference again to FIG. 1, similar to the album tracks of the aforementioned example, the event recorder component 102 can capture visual images of events 106. These images can be rendered to a user via memory recollection component 104 thereby prompting recall of additional events 106 and details that occurred within one's life. In aspects, the memory recollection component 104 can be used by a third party to review the captured images related to the events 106. As well, the user themselves can employ the memory recollection component 104 to assist in memory recall and training.

The event recorder component 102 can be wearable image capture device (e.g., camera) that keeps a digital record of the events 106 that a person experiences. The nature of the device (102) is to capture these recordings automatically, without any user intervention and therefore without any conscious effort. However, image capture can also be user-initiated or machine-initiated (e.g., by a machine-generated signal external to the event recorder) in other aspects.

As described above, a rationale behind the event recorder component 102 is that having captured a digital record of an event 106, it can subsequently be reviewed by the wearer in order to stimulate their memory (e.g., via memory recollection component 104). A suitable periodic review of this captured data generates a powerful cue which aids the consolidation of the wearer's own memory and therefore aids recall of that event 106.

Moreover, review of partial information of an event 106 can aid to recall additional detail. It is also possible that repeated use of the system 100 to record/capture and review events 106 can have a positive effect on the wearer's memory and cognitive abilities in general. More particularly, using the event recorder component 102 following a certain schedule can act to 'inoculate' the wearer from the neuro-degenerative effects of dementia or even aging in general.

Still further, the innovation contemplates and discloses aggregation of data from other image capture devices such that they can contribute data given suitable sharing rights and proximity. In operation, in one aspect, a user can subscribe to a service that stores personal image data and can augment the personal data with data from a disparate (or group of disparate) image capture device(s). For example, the system could facilitate correlation of sensor data such that any other image capture devices that happened to record the same event (e.g., as indicated by global position system (GPS) or other data) could be added to a personal view.

Essentially, the effect of multiple image capture devices would produce an rendition similar to multiple cameras on a single scene. However, in principle, a user might be interested in location over time so they might want to see all the data from image capture devices that have been in a pre-specified or defined place anytime or at a specified time or period of time. In other aspects, this image capture data can be connected to a social network (e.g., 'friends of my friends' image capture devices). Thus, it will be appreciated that use of these devices and/or associated functionality can be employed in monetization schemes, for example, earned value points for sharing your data, etc.

Figure 2:
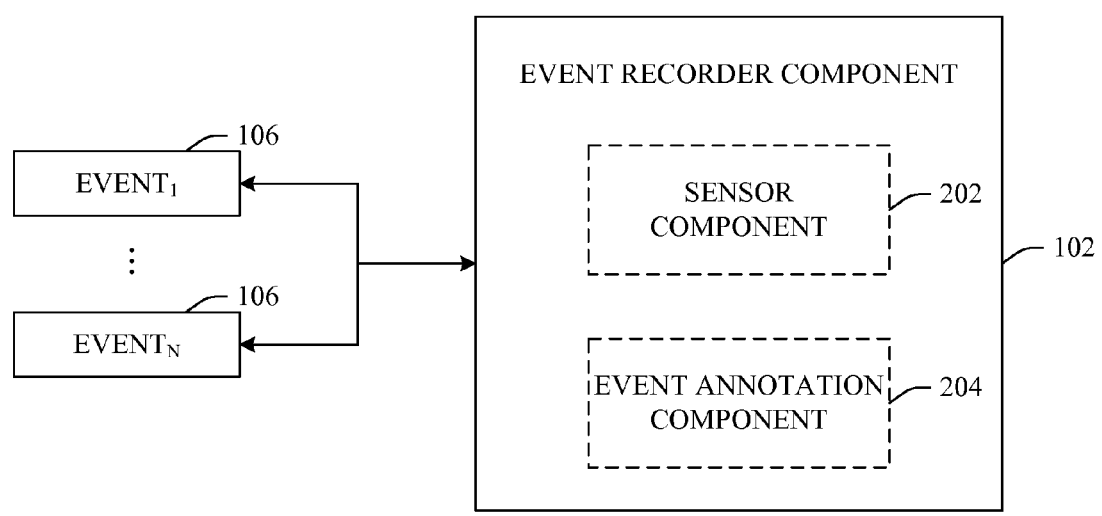
FIG. 2 illustrates a block diagram of an example event recorder component having a sensor component and an event annotation component in accordance with an aspect of the innovation.

Turning now to FIG. 2, a block diagram of an event recorder component 102 is shown. As illustrated, the event recorder component 102 can include a sensor component 202 and an optional event annotation component 204 which facilitates prompting image capture and indexing of the captured images. Essentially, the sensor component 202 can be used to trigger the capture of an image from the event recorder component 102.

Figure 3:
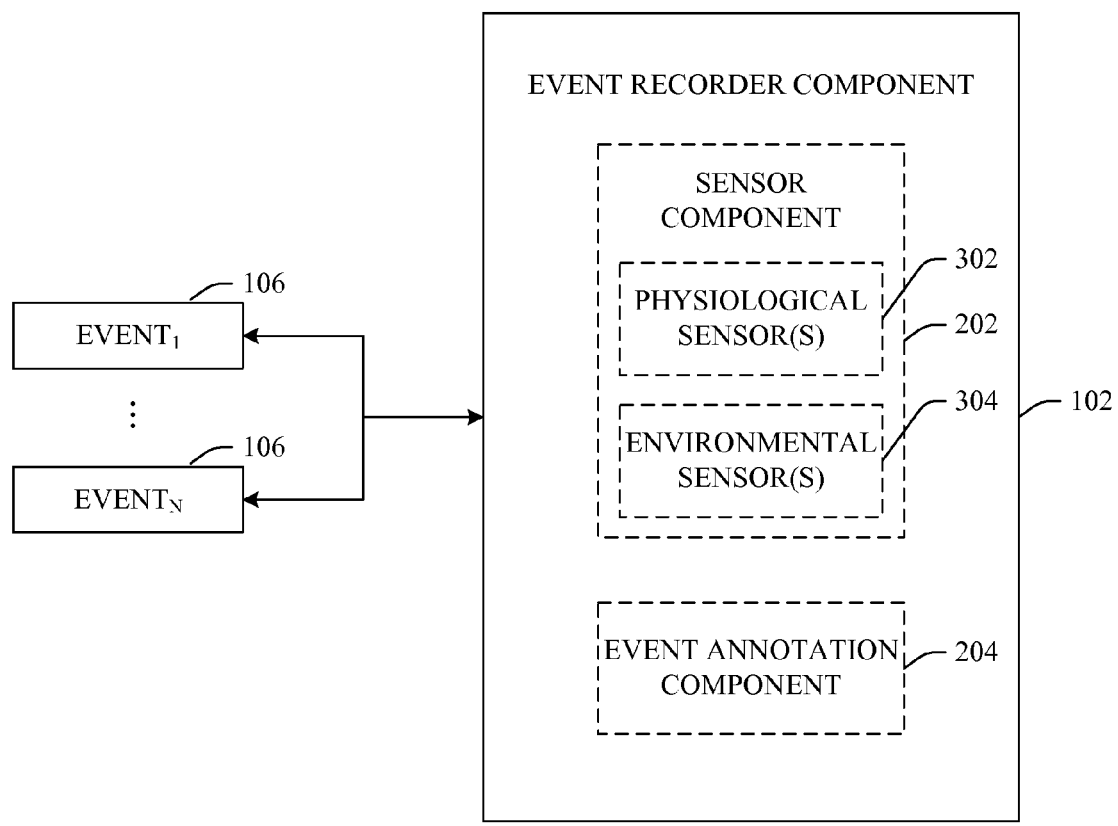
FIG. 3 illustrates a block diagram of an event recorder having a physiological sensor component and an environmental sensor component in accordance with an aspect of the innovation.

The optional event annotation component 204 can facilitate annotating (or tagging) image streams. This annotation can serve to index the images for easier location and playback. As well, the annotation can associate images with other contextual criterion (e.g., temperature, time, location). As will be appreciated, the optional event annotation can enhance usability of the captured images with regard to memory and recollection training. For example, metadata can be used to annotate particular images with regard to events, conditions and context surrounding or related to the image. This metadata can be used to locate and filter images for use in memory training and/or recollection management Referring now to FIG. 3, the sensor component 202 can include either or both physiological and/or environmental sensors (302, 304). In operation, these sensors can be used to trigger image capture as well as to gather information and data to be used in annotating images. For instance, when a specific threshold is reached, an image or series of images can be automatically captured and annotated with the data related to the triggering threshold.

In one example, the event recorder component 102 can monitor physiological criterion such as heart rate, blood pressure, body temperature, blood sugar, blood/alcohol concentration, etc. In operation, when a user's or wearer's heart rate rises above a predetermined level, the event recorder component can automatically prompt capture of images. Similarly, the event annotation component 204 can be used to annotate the captured images with specified data related to the physiological sensor(s) (e.g., heart rate). In this manner, a better understanding of events leading to a medical condition can be obtained.

Similarly, environmental sensors 304 can be used to trigger image capture as well as to provide annotation criteria. For example, sensors can be employed to automatically trigger image capture upon changes in motion, location, temperature, lighting, etc. These changes can be complimented by a detection of a relatively stable period that can be captured by an accelerometer. In addition to triggering capture of images, these environmental criteria can be used to annotate (or index) the captured images in order to assist in playback and memory training.

One key issue addressed by this specification is the application of the event recorder component 102 to improve failing memories in patients with a diagnosed memory condition such as acquired brain injury or neurodegenerative disease such as Alzheimer's disease. In conjunction with this invention, trials have been conducted with an acquired brain injury patient (e.g., limbic encephalitis which resulted in severe amnesia) and with early Alzheimer's disease patients. Accordingly, increased memory function was experienced thereby reducing the effect(s) of the disease and/or condition.

Much of the value of event recorder component 102 is in the chronological, time-compressed, first-person nature of the image data, and the fact that the data is collected without any conscious effort or intervention on the part of the wearer. Moreover, images can be captured without introducing any interruptions in the activities performed or with interruption of the people interacted with during the course of the event.

The process of using an event recorder component 102 to record an event 106 (or portion thereof) is very straightforward from the wearer's point of view. In other words, all the wearer needs to do is to remember (or decide) to put on and switch on the camera at the start of the event (e.g., start of the day). As described above, the record can be made with no further conscious effort or intervention on the wearer's part or by other people they interact with. For instance, the image capture can be automatic or prompted by sensory technology (as described supra). Similarly, the granularity can be predetermined or determined as a function of preference or data gathered via sensory technologies (302, 304).

Capturing image sequences from the wearer's point of view is very different and has benefits apart from conventional techniques. For example, using a standard digital stills camera or a video camera requires cognitive overhead on the part of the recorder—they have to continually take themselves 'out of the moment' in order to maintain the record. Also, in these conventional systems, the recording process is quite visible to others which can oftentimes lead to people continually taking themselves out of the moment as well. Also, the periodic still images recorded by the event recorder component 102 are less invasive of privacy than continuous video. Further, it will be understood that the alternative of keeping a detailed written diary during an event for subsequent review can be extremely inaccurate and tiresome.

Moreover, the process of reviewing data captured via the event recorder component 102 can be quite enjoyable for the viewer. This contrasts with reviewing a written diary, which is considered to be very burdensome, and with reviewing video or individual digital stills which is also frequently considered quite dull. It will be understood that the image sequence captured by the event recorder component 102 tells somewhat of a story of an event which in turn captivates the viewer thereby prompting recollection.

Figure 4:
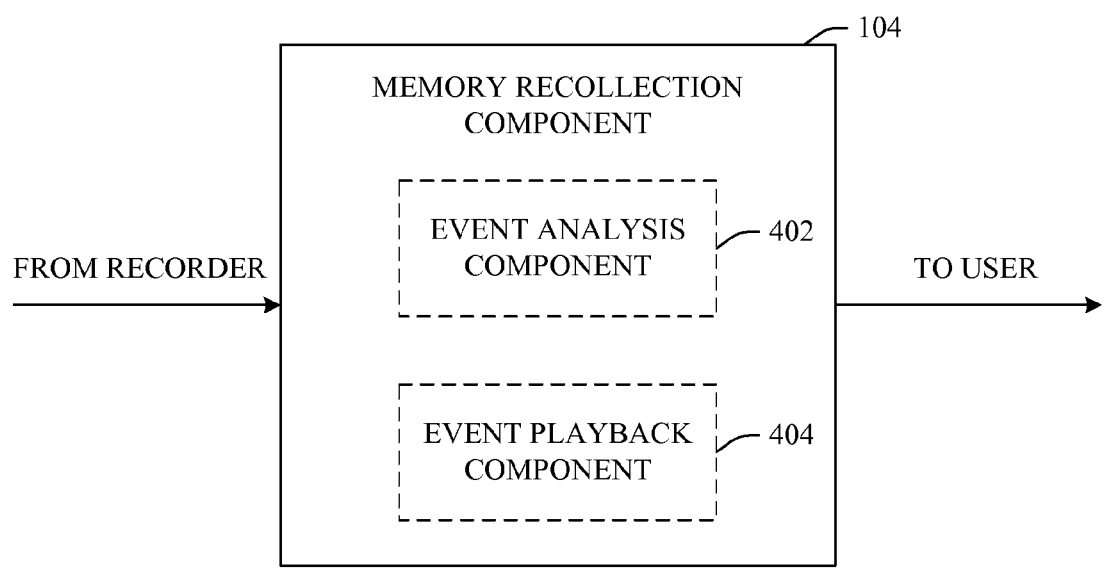
FIG. 4 illustrates an example memory recollection component having an event analysis component and an event playback component in accordance with an aspect of the innovation.

Turning now to FIG. 4, a block diagram of a memory recollection component 104 is shown to include an event analysis component 402 and an event playback component 404. Effectively, the analysis performed by the event analysis component 402 can range from a simple time-based/counter analysis of frames within a sequence to a very comprehensive analysis of the images and annotations associated therewith. In a simple scenario, the event analysis component 402 can be employed to locate images based upon a desired time of capture.

For example, if a memory training session is directed to a specific meeting within a day's captured events, a viewer can specify the time of the meeting whereby the event analysis component 402 can locate the beginning of this sub-event within the day's sequence. This sub-event can be used to prompt memory recollection of the complete event (e.g., meeting) and likewise can be used to prompt additional recollection of details not necessarily captured in the image sequence. Subsequently, the event playback component 404 can be used to display the images to a viewer in the course of memory training, recollection and/or enhancement.

As described supra, sensory technologies can be employed to capture environmental and physiological criteria associated with an image capture sequence. By way of example, sensors can be used to capture time of day, ambient temperature, external noises, etc. Thus, the event analysis component 402 can identify this information from the sequence and translate/transfer the information to the event playback component 404. Thereafter, the event playback component 404 can be employed to recreate the actual environment of the event in order to assist in prompting recollection. In other words, the event playback component 404 can be used to simulate the ambient temperature and external noises (e.g., thunder, train, clock tolls, overhead paging system) experienced during an event in order to enhance recall and training.

It is to be understood that enhancing (e.g., annotating) the replay image of data with other environmental and physiological data recorded during the event can have a further therapeutic effect. Other examples of data captured might be location (e.g., through global positing system (GPS)); physiological data might include electrocardiogram (ECG) data such as heart rate, or skin conductance data, etc. Although specific examples of ancillary and/or contextual data are given, it is to be understood that other examples exist and are to be included within the scope of this disclosure and claims appended hereto.

Essentially, whether used for real-life playback or for reference, it is to be understood that additional data such as the environmental and physiological data mentioned above can assist in segmenting a recorded image sequence. Such segmentation can be particularly useful for image sequence review, since it makes the review more manageable.

It will be appreciated that human memories are believed by many experts to be stored in discrete 'chunks' and therefore chunking the image sequence in an analogous manner could well improve the beneficial effect of innovation. In disparate examples, chunking can be based upon event time, type, place, subject, etc. Essentially, most any criteria can be used in order to define chunks related to an image sequence. Regardless of the mechanisms used for chunking, it is to be understood that there may be particular ways to use sensor data (and to process in the image data) to segment image sequences in ways that produce more manageable chunks and therefore show improved ability for patients to recall.

Figure 5:
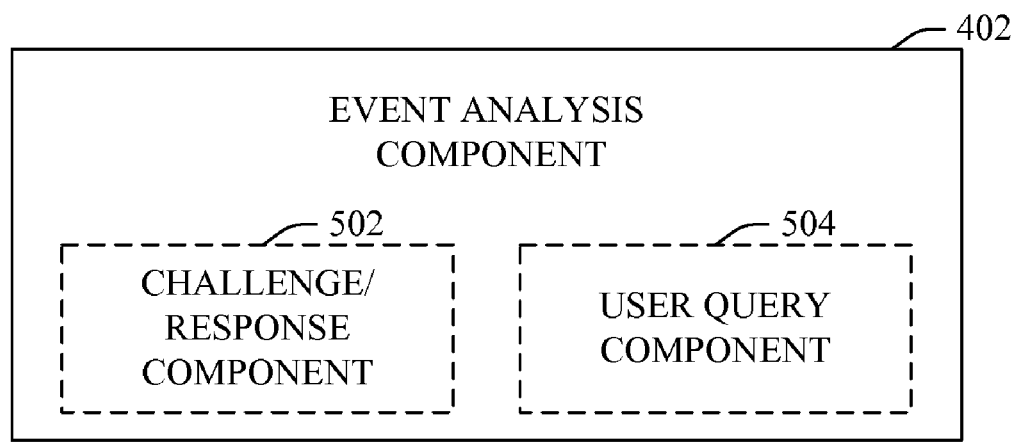
FIG. 5 illustrates an example event analysis component having a challenge/response component and a user query component in accordance with an aspect of the innovation.

Referring now to FIG. 5, a block diagram of an example event analysis component 402 is shown. Generally, the event analysis component 402 can include a challenge/response component 502 and a user query component 504. Although these components (502, 504) as shown to be co-located within the event analysis component 402, it is to be understood that each of these components (502, 504) are standalone components and can be present without the other.

In operation, the event analysis component 402 can employ the annotations as well as pattern/image recognition technologies to evaluate a captured image sequence. Once evaluated, an index of chunks or segments can be generated and used to effectuate memory training and enhancement. For example, a user can be quizzed or can likewise question the system for details captured via an event sequence. It is also to be appreciated that, in other aspects, an image sequence can be manually indexed.

The challenge/response component 502 can be used to automatically quiz a patient/viewer about an event or series of events. For instance, once the automated indexing is complete, the system can quiz (or challenge) a user for details such as, 'what mode of travel was used to get to the opera?' In turn, the patient/view would respond with the appropriate mode of travel, e.g., train.

Similarly, the user query component 504 can be employed by a user to extract details associated with an event. For instance, if a user remembers going to the opera but does not recall how they arrived at the opera, the user can query the system to determine that they took the train. Over time, this challenge/response and query systems can assist in training and 'working out' the brain in order to enhance memory and memory recall function.

Figure 6:
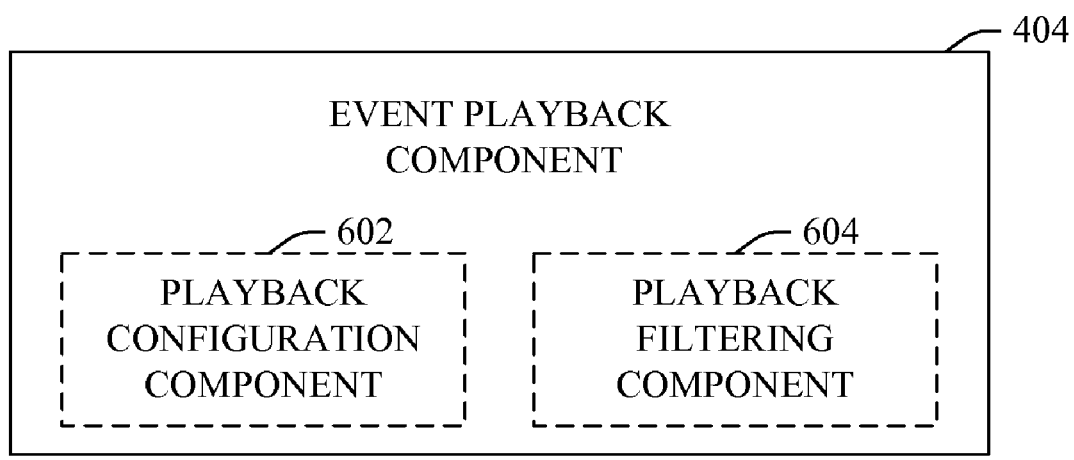
FIG. 6 illustrates an example event playback component having a playback configuration component and a playback filtering component in accordance with an aspect of the innovation.

FIG. 6 illustrates a block diagram of an event playback component 404 having a playback configuration component 602 and a playback filtering component 604. Each of these components (602, 604) can be used to control playback of an image sequence, for example, in the course of memory training and/or therapy.

The playback configuration component 602 can enable playback of an image or sequence of images to be configured for a specific device or display apparatus. In one example, the playback configuration component 602 can modify image data as necessary for display on a portable device such as a mobile phone, smartphone, personal data assistant (PDA) or the like. Similarly, the innovation can configure image data for display via a desktop monitor, laptop monitor, television, or the like.

The filtering component 604 can automatically redact or mask portions of an event sequence prior to playback. For example, the playback filtering component 604 can mask images captured in areas where privacy is of concern, e.g., bathrooms, showers, etc. Additionally, the playback filtering component 604 can be trained to filter images prior to recording or at the time of playback. This training can be rule-based or effectuated by a machine learning and/or reasoning (MLR) component as shown in FIG. 7 that follows.

This pre-view or post-view filtering can accomplish at least two goals, privacy and therapy. As described above, privacy may be of concern and can therefore be considered prior to capturing images. Sensory technology can be used to assist in the determination if images should be filtered or masked.

As well, in the case of therapy, the system can automatically filter segments (or chunks) of image data in order to prompt or promote memory recall/training. In this scenario, the system can automatically mask portions of events that are statistically or historically determined to be difficult for a patient as a function of a particular illness, age, injury, etc.

Figure 7:
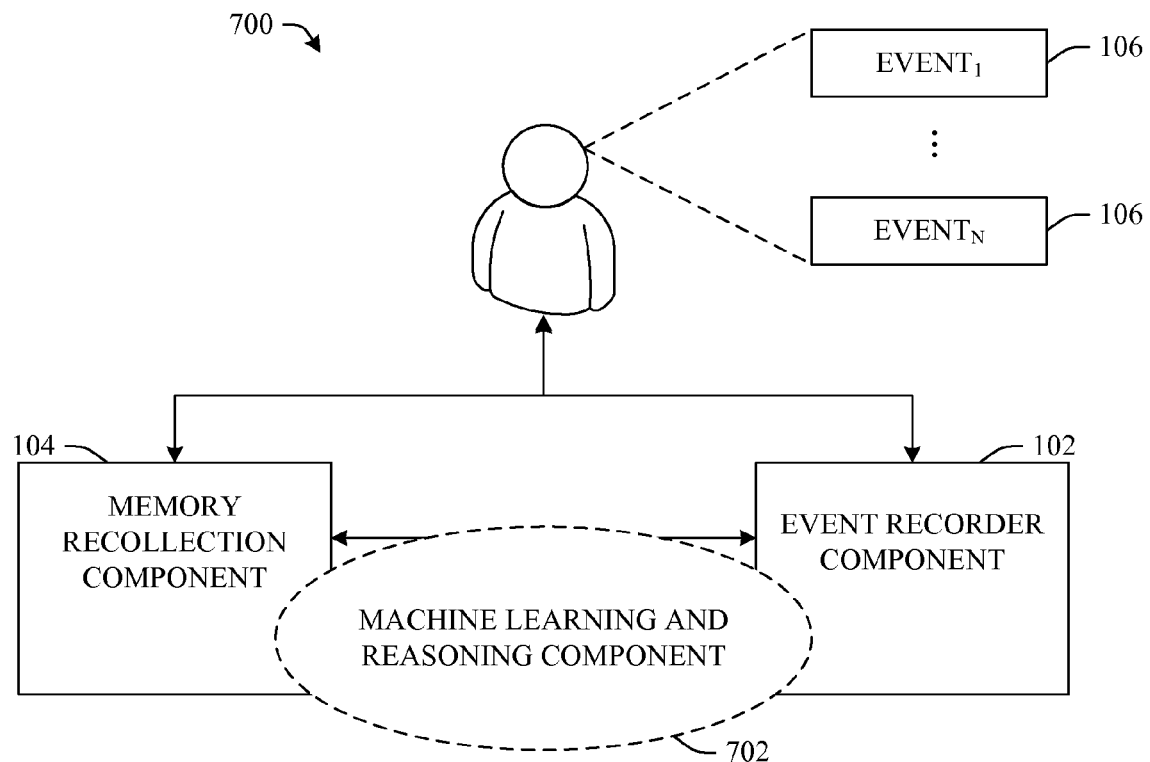
FIG. 7 illustrates an architecture including a machine learning and reasoning component that can automate functionality in accordance with an aspect of the innovation.

FIG. 7 illustrates a system 700 that employs machine learning and reasoning (MLR) component 702 which facilitates automating one or more features in accordance with the subject innovation. The subject innovation (e.g., in connection with prompting image capture) can employ various MLR-based schemes for carrying out various aspects thereof. For example, a process for determining when to trigger the event recorder component 102 to begin capture can be facilitated via an automatic classifier system and process. Moreover, MLR techniques can be employed to control playback (e.g., filtering) of images based upon certain data related to an event and a wearer (e.g., context). As illustrated, it is to be understood that MLR functionality can be integrated within either (or both) of the event recorder component 102 and/or the memory recollection component 104.

A classifier is a function that maps an input attribute vector, $x=(x1, x2, x3, x4, xn)$, to a confidence that the input belongs to a class, that is, $f(x)=confidence(class)$. Such classification can employ a probabilistic and/or statistical-based analysis (e.g., factoring into the analysis utilities and costs) to prognose or infer an action that a user desires to be automatically performed.

A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated from the subject specification, the subject innovation can employ classifiers that are explicitly trained (e.g., via a generic training data) as well as implicitly trained (e.g., via observing user behavior, receiving extrinsic information). For example, SVM's are configured via a learning or training phase within a classifier constructor and feature selection module. Thus, the classifier(s) can be used to automatically learn and perform a number of functions, including but not limited to determining according to a predetermined criteria when to trigger capture of an image, when to prohibit capture of an image, how to display an image, when to mask an image during playback, what granularity to capture images (e.g., number of frames per second), etc.

Figure 8:
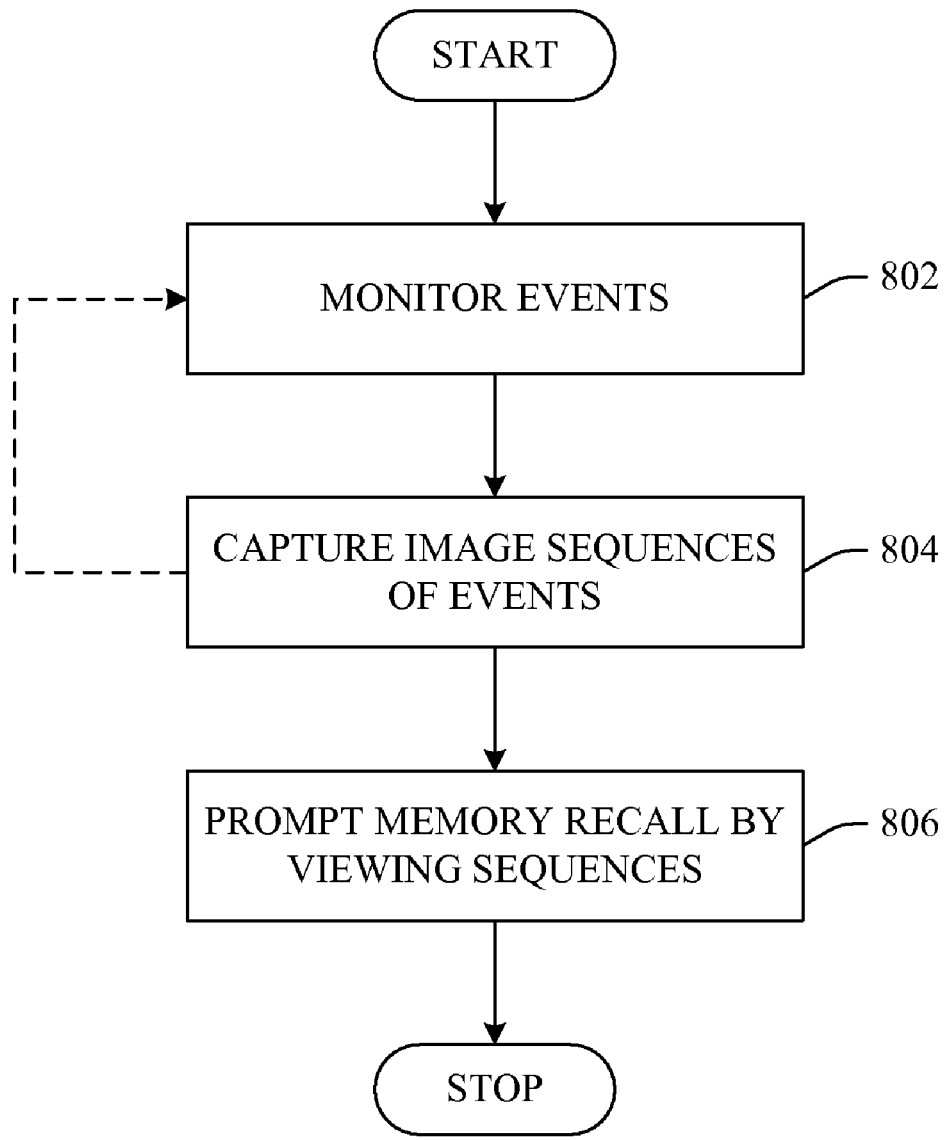
FIG. 8 illustrates an exemplary flow chart of procedures that facilitate enhancing or rehabilitating memory function via viewing image sequences in accordance with an aspect of the innovation.

FIG. 8 illustrates a methodology of employing a sequence of event images in training memory in accordance with an aspect of the innovation. While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

At 802, events can be monitored. In examples, an event can be period of time (e.g., hour, day, week, month, year) or a specific activity (e.g., meeting with friends, business meeting, vacation, visit to a grocery store). It is to be appreciated that most any period of time or activity can be quantified into an event, or group of events.

At 804, image sequences of events are captured. As described above, the granularity of the capture of images can be based upon the nature of the neurological disease, condition and/or injury. Thus, the granularity can be preprogrammed or inferred based upon the appropriate disease, condition and/or injury as a function of a wearer's physiological and/or environmental context. As illustrated by the dashed line in FIG. 8, in an alternate example, events can be monitored and captured (e.g., in the form of event sequences) recursively. In other words, analysis and/or use of the captured images can be performed at any time (e.g., after all or a portion of images are captured).

Memory recall can be prompted by viewing sequences (or portions thereof) at 806. In other words, as described above, it will be understood that viewing an image sequence can prompt recall and thereafter train the memory to remember events and details related thereto. In other words, the methodology described in FIG. 8 can be employed to 'work-out' the brain of individuals with neurological diseases and/or acquired head injury. Moreover, although the scenarios are directed to assisting and increasing memory function in individuals that suffer from some form of deteriorated memory function, it is to be understood that the event images (and sequences thereof) of the subject innovation can be employed to increase memory function of individuals that do not necessarily suffer from any form of dementia. Rather, the viewing of images and sequences can be used to increase even 'normal' memory function.

Figure 9:
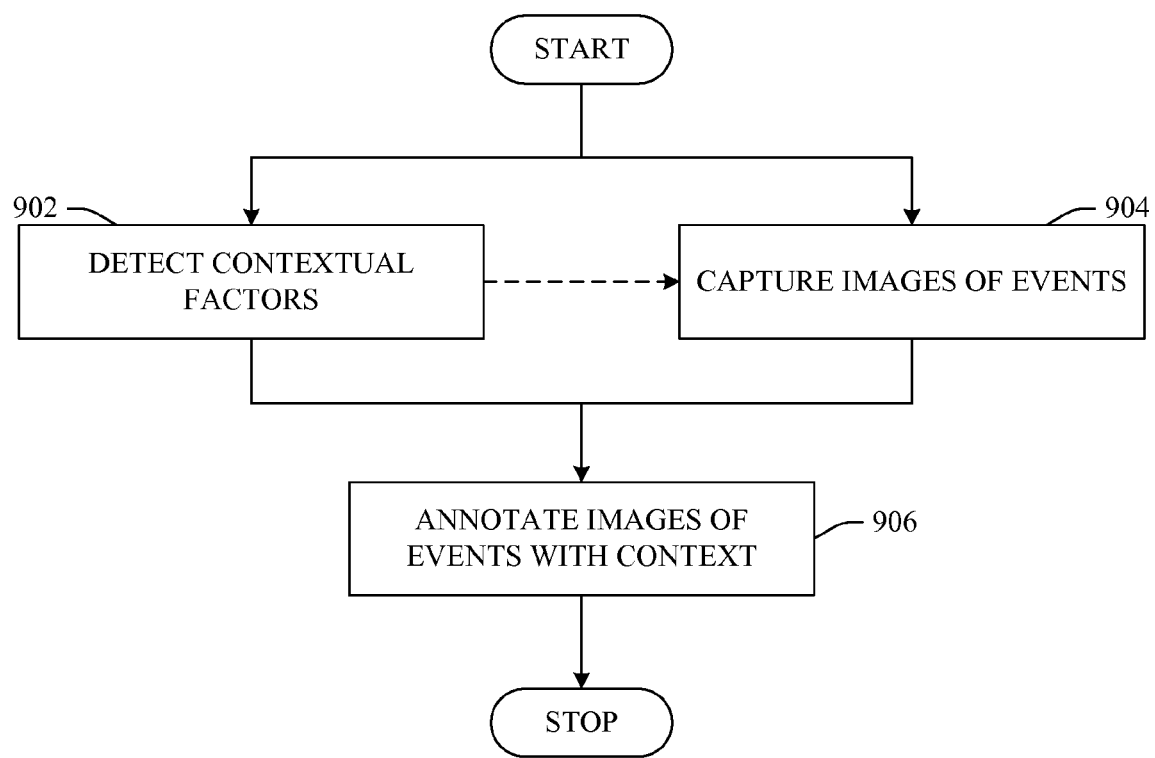
FIG. 9 illustrates an exemplary flow chart of procedures that facilitate annotating image sequences with context data (e.g., physiological, environmental) in accordance with an aspect of the innovation.

Referring now to FIG. 9, there is illustrated a methodology of annotating images in accordance with the innovation. Specifically, at 902, contextual factors related to an individual or event can be detected. For instance, as described supra, physiological and/or environmental sensors can be employed to monitor criteria related to an individual and/or event.

Images related to an event (or sequence of events) can be captured at 904. The capture of these images can be triggered as a function of the contextual data/factors gathered at 902. Once captured, the images and/or sequences of images can be annotated with contextual data (and other sensor-provided data) at 906. These annotations can provide additional data to assist in describing and/or explaining an event in the course of training/therapy. Additionally, as will be described with reference to the methodology of FIG. 10, the annotations can be used to recreate an environment to mimic actual conditions during an event.

Figure 10:
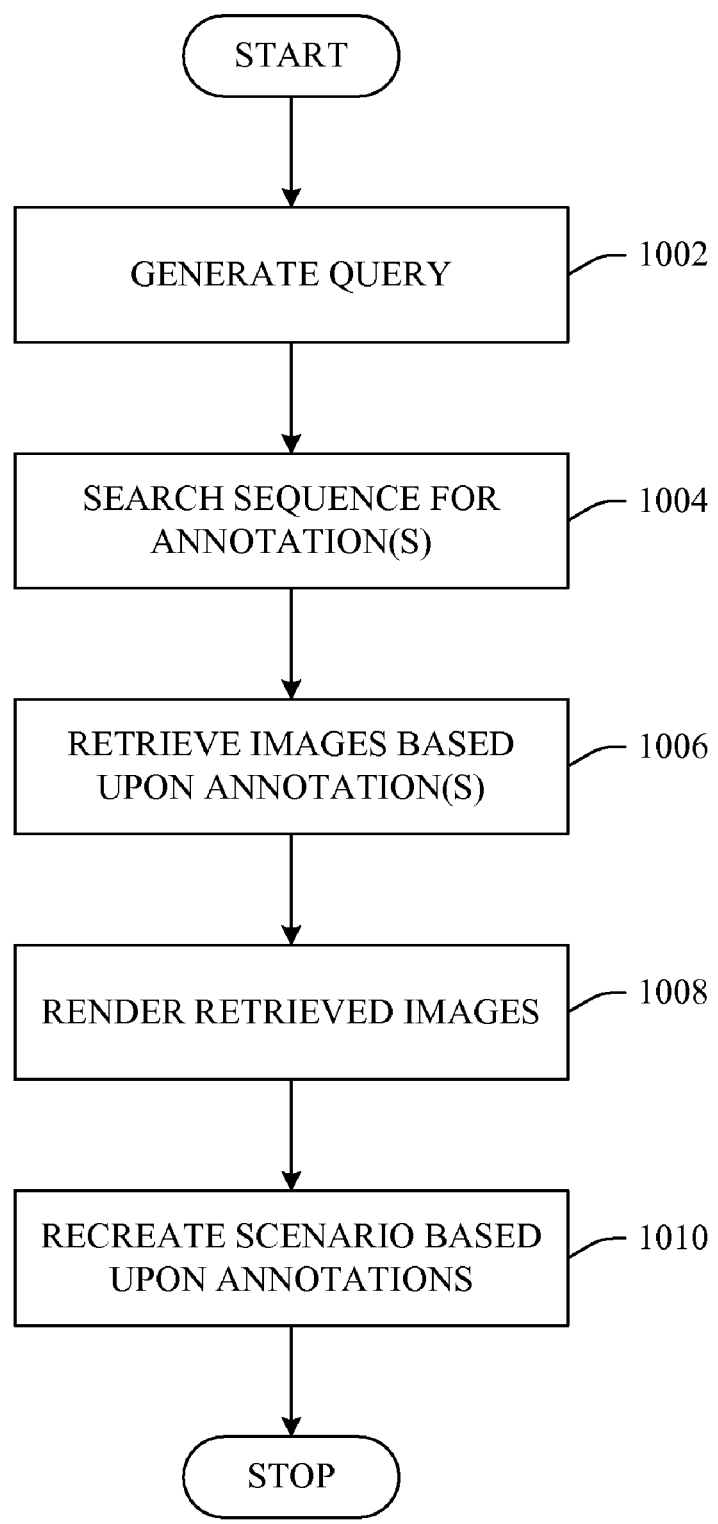
FIG. 10 illustrates an exemplary flow chart of procedures that facilitate employing annotations to enhance playback of captured images in accordance with an aspect of the innovation.

With reference now to FIG. 10, a methodology of searching for a specific event and recreating an environment of the event in accordance with the innovation is shown. Initially, at 1002, a query can be generated. This query can be specific to identify a point within an event or general to identify an event as a whole.

A search can be conducted at 1004 in order to locate desired images and/or sequences of images. In aspects, pattern and audio recognition mechanisms can be employed in order to search for and locate desired images and/or sequences that match a defined query. Similarly, these pattern and/or audio recognition systems can be employed to pre-annotate images thereafter effectuating the search and subsequent retrieval at 1006. By way of example, the event analysis component (e.g., 402 of FIG. 4) can be equipped with these recognition systems in order to automate location and/or annotation based upon content of the images.

Once retrieved, the images can be rendered at 1008 in the course of therapy, training, rehabilitation, 'work-out', etc. Still further, the actual scenario of the event at the time of the image sequence capture can be recreated based upon annotations at 1010. For example, ambient temperature can be matched, ancillary sounds (e.g., train, clock) can be generated, etc. in order to facilitate a reality experience thereby enhancing recollection effect.

Figure 11:
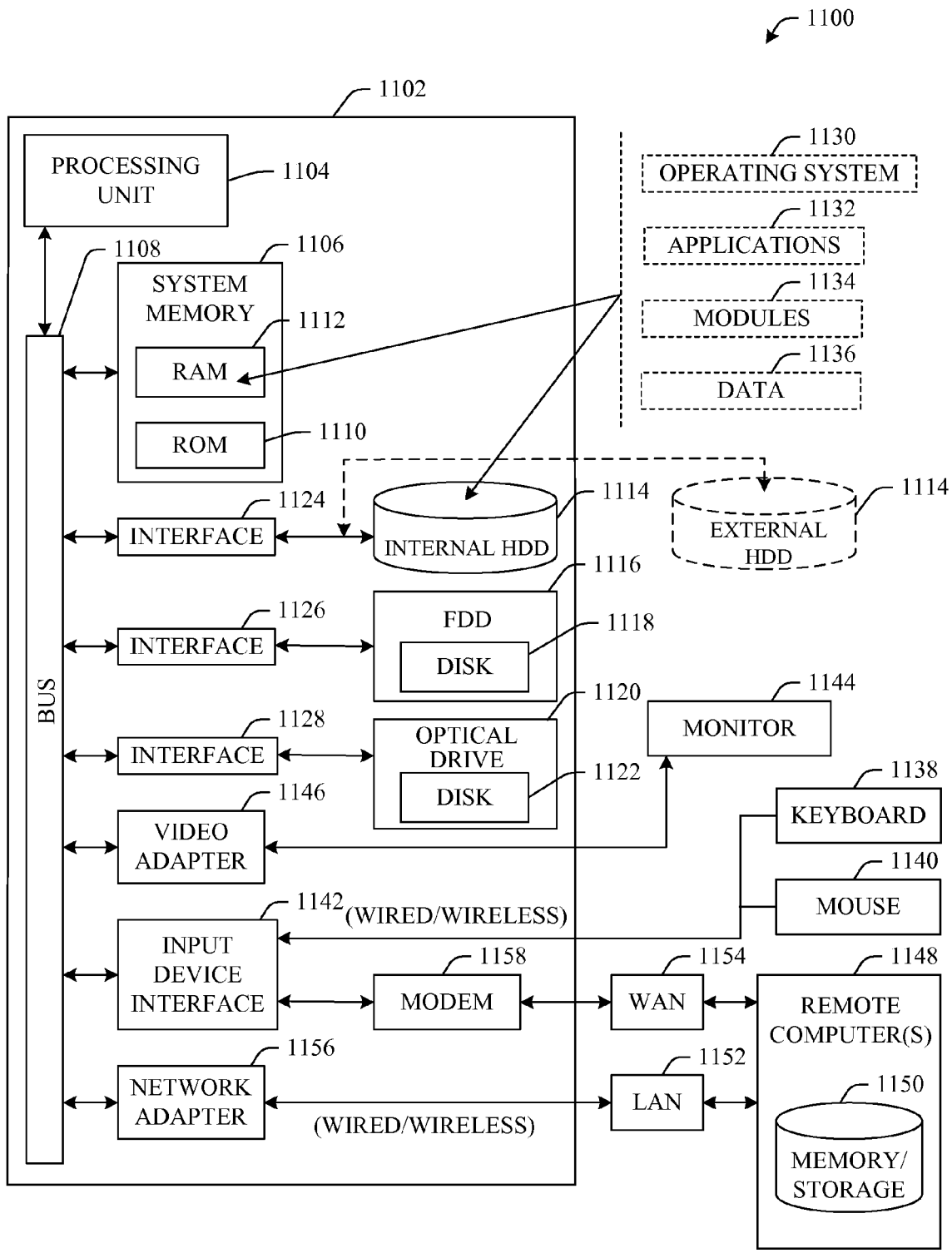
FIG. 11 illustrates a block diagram of a computer operable to execute the disclosed architecture.

Referring now to FIG. 11, there is illustrated a block diagram of a computer operable to execute the disclosed architecture of capturing image sequences and/or employing image sequences in memory training and rehabilitation. In order to provide additional context for various aspects of the subject innovation, FIG. 11 and the following discussion are intended to provide a brief, general description of a suitable computing environment 1100 in which the various aspects of the innovation can be implemented. While the innovation has been described above in the general context of computer-executable instructions that may run on one or more computers, those skilled in the art will recognize that the innovation also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 11, the exemplary environment 1100 for implementing various aspects of the innovation includes a computer 1102, the computer 1102 including a processing unit 1104, a system memory 1106 and a system bus 1108. The system bus 1108 couples system components including, but not limited to, the system memory 1106 to the processing unit 1 104. The processing unit 1104 can be any of various commercially available processors. Dual microprocessors and other multi-processor architectures may also be employed as the processing unit 1104.

The system bus 1108 can be any of several types of bus structure that may further interconnect to a memory bus (with or without a memory controller), a peripheral bus, and a local bus using any of a variety of commercially available bus architectures. The system memory 1106 includes read-only memory (ROM) 1110 and random access memory (RAM) 1112. A basic input/output system (BIOS) is stored in a non-volatile memory 1110 such as ROM, EPROM, EEPROM, which BIOS contains the basic routines that help to transfer information between elements within the computer 1102, such as during start-up. The RAM 1112 can also include a high-speed RAM such as static RAM for caching data.

The computer 1102 further includes an internal hard disk drive (HDD) 1114 (e.g., EIDE, SATA), which internal hard disk drive 1114 may also be configured for external use in a suitable chassis (not shown), a magnetic floppy disk drive (FDD) 1116, (e.g., to read from or write to a removable diskette 1118) and an optical disk drive 1120, (e.g., reading a CD-ROM disk 1122 or, to read from or write to other high capacity optical media such as the DVD). The hard disk drive 1114, magnetic disk drive 1116 and optical disk drive 1120 can be connected to the system bus 1108 by a hard disk drive interface 1124, a magnetic disk drive interface 1126 and an optical drive interface 1128, respectively. The interface 1124 for external drive implementations includes at least one or both of Universal Serial Bus (USB) and IEEE 1394 interface technologies. Other external drive connection technologies are within contemplation of the subject innovation.

The drives and their associated computer-readable media provide nonvolatile storage of data, data structures, computer-executable instructions, and so forth. For the computer 1102, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the innovation.

A number of program modules can be stored in the drives and RAM 1112, including an operating system 1130, one or more application programs 1132, other program modules 1134 and program data 1 136. All or portions of the operating system, applications, modules, and/or data can also be cached in the RAM 1112. It is appreciated that the innovation can be implemented with various commercially available operating systems or combinations of operating systems.

A user can enter commands and information into the computer 1102 through one or more wired/wireless input devices, e.g., a keyboard 1138 and a pointing device, such as a mouse 1140. Other input devices (not shown) may include a microphone, an IR remote control, a joystick, a game pad, a stylus pen, touch screen, or the like. These and other input devices are often connected to the processing unit 1104 through an input device interface 1142 that is coupled to the system bus 1108, but can be connected by other interfaces, such as a parallel port, an IEEE 1394 serial port, a game port, a USB port, an IR interface, etc.

A monitor 1144 or other type of display device is also connected to the system bus 1108 via an interface, such as a video adapter 1146. In addition to the monitor 1144, a computer typically includes other peripheral output devices (not shown), such as speakers, printers, etc.

The computer 1102 may operate in a networked environment using logical connections via wired and/or wireless communications to one or more remote computers, such as a remote computer(s) 1148. The remote computer(s) 1148 can be a workstation, a server computer, a router, a personal computer, portable computer, microprocessor-based entertainment appliance, a peer device or other common network node, and typically includes many or all of the elements described relative to the computer 1102, although, for purposes of brevity, only a memory/storage device 1150 is illustrated. The logical connections depicted include wired/wireless connectivity to a local area network (LAN) 1152 and/or larger networks, e.g., a wide area network (WAN) 1154. Such LAN and WAN networking environments are commonplace in offices and companies, and facilitate enterprise-wide computer networks, such as intranets, all of which may connect to a global communications network, e.g., the Internet.

When used in a LAN networking environment, the computer 1102 is connected to the local network 1152 through a wired and/or wireless communication network interface or adapter 1156. The adapter 1156 may facilitate wired or wireless communication to the LAN 1152, which may also include a wireless access point disposed thereon for communicating with the wireless adapter 1156.

When used in a WAN networking environment, the computer 1102 can include a modem 1158, or is connected to a communications server on the WAN 1154, or has other means for establishing communications over the WAN 1154, such as by way of the Internet. The modem 1158, which can be internal or external and a wired or wireless device, is connected to the system bus 1108 via the serial port interface 1142. In a networked environment, program modules depicted relative to the computer 1102, or portions thereof, can be stored in the remote memory/storage device 1150. It will be appreciated that the network connections shown are exemplary and other means of establishing a communications link between the computers can be used.

The computer 1102 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

Figure 12:
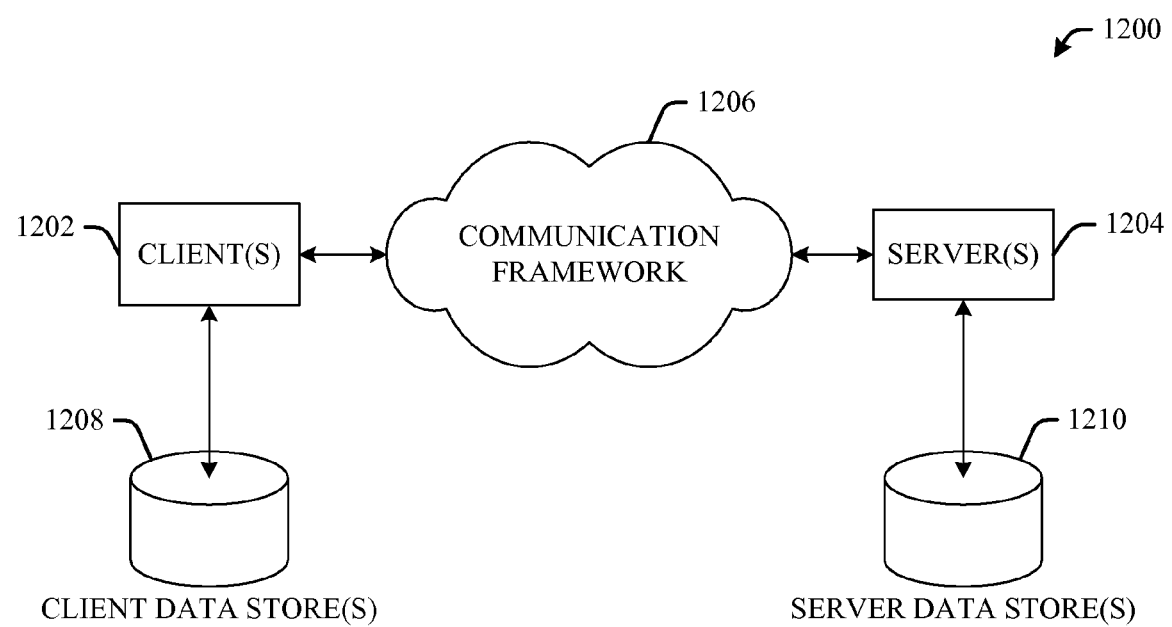
FIG. 12 illustrates a schematic block diagram of an exemplary computing environment in accordance with the subject innovation.

Referring now to FIG. 12, there is illustrated a schematic block diagram of an exemplary computing environment 1200 in accordance with the subject innovation. The system 1200 includes one or more client(s) 1202. The client(s) 1202 can be hardware and/or software (e.g., threads, processes, computing devices). The client(s) 1202 can house cookie(s) and/or associated contextual information by employing the innovation, for example.

The system 1200 also includes one or more server(s) 1204. The server(s) 1204 can also be hardware and/or software (e.g., threads, processes, computing devices). The servers 1204 can house threads to perform transformations by employing the innovation, for example. One possible communication between a client 1202 and a server 1204 can be in the form of a data packet adapted to be transmitted between two or more computer processes. The data packet may include a cookie and/or associated contextual information, for example. The system 1200 includes a communication framework 1206 (e.g., a global communication network such as the Internet) that can be employed to facilitate communications between the client(s) 1202 and the server(s) 1204.

Communications can be facilitated via a wired (including optical fiber) and/or wireless technology. The client(s) 1202 are operatively connected to one or more client data store(s) 1208 that can be employed to store information local to the client(s) 1202 (e.g., cookie(s) and/or associated contextual information). Similarly, the server(s) 1204 are operatively connected to one or more server data store(s) 1210 that can be employed to store information local to the servers 1204.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A computer-implemented system configured to facilitate autobiographical memory recall, the computer-implemented system comprising:
    an event recorder device configured to capture images associated with an event;
    an event annotation component configured to automatically annotate captured images with context data associated with the captured images;
    a playback filtering component configured to filter the captured images based on the context data associated with the captured images;
    a machine learning and reasoning component configured to automate actions of the event recorder device and the playback filtering component for privacy, the machine learning and reasoning component employing one or more of probabilistic-based analysis and statistical-based analysis of observed events to automatically learn when to prohibit capture of images and when to mask portions of captured images prior to playback; and
    a memory recollection component configured to display a subset of the captured images for assisting memory recall of the event.

2. The computer-implemented system of claim 1, further comprising an event analysis component configured to locate the subset of the captured images as a function of a portion of the event.

3. The computer-implemented system of claim 1, further comprising a challenge/response component configured to locate the subset of the captured images as a function of a user response to a system-generated challenge.

4. The computer-implemented system of claim 1, further comprising a user query component configured to facilitate generation of a user-defined query, the subset of the captured images being located as a function of the user-defined query.

5. The computer-implemented system of claim 1, further comprising an event playback component configured to of the subset of the captured images.

6. The computer-implemented system of claim 5, further comprising a playback configuration component configured to format the subset of the captured images playback.

7. The computer-implemented system of claim 1, wherein images of the subset that are captured in areas designated as private are masked.

8. The computer-implemented system of claim 1 wherein the machine learning and reasoning component comprises a support vector machine classifier.

9. The computer-implemented system of claim 1, further comprising a sensor component configured to trigger capture of images by the event recorder device.

10. The computer-implemented system of claim 9, wherein the sensor component is at least one of an environmental sensor component or a physiological sensor component.

11. The computer-implemented system of claim 1, wherein the event recorder device is configured to capture a video clip.

12. The computer-implemented system of claim 1, wherein the event recorder device is configured to capture images from a point of view of a wearer of the event recorder device.

13. The computer-implemented system of claim 1, wherein the subset of the captured images is displayed via a time-compressed, slide show format.

14. A computer-implemented method for facilitating autobiographical memory recall, the computer-implemented method comprising:
    executing a machine learning and reasoning component by a processor of a computer system, the computer system configured to capture images and filter captured images, the machine learning and reasoning component including computer-executable instructions to automate actions of the computer system for privacy, the machine learning and reasoning component employing one or more of probabilistic-based analysis and statistical-based analysis of observed events to automatically learn when to prohibit capture of images and when to mask portions of captured images prior to playback; and
    performing, by the computer system, operations comprising:
        automatically capturing images associated with an event;
        automatically annotating captured images with context data associated with the captured images;
        automatically filtering the captured images based on the context data associated with the captured images; and
        rendering a subset of the captured images for assisting memory recall of the event.

15. The computer-implemented method of claim 14, wherein the computer system captures a video stream including the subset of the captured images.

16. The computer-implemented method of claim 14, wherein the computer system captures images from a point of view of a user.

17. The computer-implemented method of claim 14, wherein the subset of the captured images is rendered in a time-compressed format.

18. A computer-readable storage medium that does not consist of a signal, the computer-readable storage medium storing computer-executable instructions that, when executed by a computing device, cause the computing device to perform a method for facilitating autobiographical memory recall, the computing device configured to capture images and filter captured images, the method comprising:

executing a machine learning and reasoning component to automate actions of the computing device for privacy, the machine learning and reasoning component employing one or more of probabilistic-based analysis and statistical-based analysis of observed events to automatically learn when to prohibit capture of images and when to mask portions of captured images prior to playback;

automatically capturing images associated with an event;

automatically annotating captured images with context data associated with the captured images;

automatically filtering the captured images based on the context data associated with the captured images; and rendering a subset of the captured images for assisting memory recall of the event.

19. The computer-readable storage medium of claim 18, wherein the subset of the captured images is rendered in a time-compressed format.

20. The computer-implemented method of claim 14, further comprising sharing the subset of the captured images with members of a social network of a user of the computer system.

\* \* \* \* \*